(12) United States Patent
Swiss

(10) Patent No.: US 11,199,539 B2
(45) Date of Patent: Dec. 14, 2021

(54) METHODS, COMPOSITIONS AND DEVICES FOR IMPROVING THE SENSITIVITY OF ASSAYS

(71) Applicant: WALKILL CONCEPTS, INC., Rancho Santa Fe, CA (US)

(72) Inventor: Gerald F. Swiss, Rancho Sante Fe, CA (US)

(*) Notice: Subject to any disclaimer, the term of this patent is extended or adjusted under 35 U.S.C. 154(b) by 121 days.

(21) Appl. No.: 15/999,586

(22) PCT Filed: Feb. 15, 2017

(86) PCT No.: PCT/US2017/017988
§ 371 (c)(1),
(2) Date: Aug. 16, 2018

(87) PCT Pub. No.: WO2017/142956
PCT Pub. Date: Aug. 24, 2017

(65) Prior Publication Data
US 2019/0212336 A1    Jul. 11, 2019

Related U.S. Application Data

(60) Provisional application No. 62/296,059, filed on Feb. 16, 2016, provisional application No. 62/456,020, filed on Feb. 7, 2017.

(51) Int. Cl.
*G01N 33/543* (2006.01)
*G01N 33/53* (2006.01)
*G01N 33/569* (2006.01)

(52) U.S. Cl.
CPC ... *G01N 33/54393* (2013.01); *G01N 33/5306* (2013.01); *G01N 33/543* (2013.01);
(Continued)

(58) Field of Classification Search
CPC ....... G01N 33/54393; G01N 33/54333; G01N 33/58; G01N 33/54306; G01N 33/543;
(Continued)

(56) References Cited

U.S. PATENT DOCUMENTS 5,340,748 A * 8/1994 Baugher .......... G01N 33/54306
435/7.93
5,527,686 A    6/1996 Fitzpatrick et al.
(Continued)

FOREIGN PATENT DOCUMENTS

WO    WO-2017/142956 A1    8/2017

OTHER PUBLICATIONS

M. Nisenvitch, M.A. Firer. The solid phase in affinity chromatography: strategies for antibody attachment. J. Biochem. Biophys. Methods. vol. 49. pp. 467-480. 2001 (Year: 2001).*
(Continued)

*Primary Examiner* — Christopher L Chin
(74) *Attorney, Agent, or Firm* — Mintz, Levin, Cohn, Ferris, Glovsky and Popeo, P.C.

(57) ABSTRACT

This application relates to assays, devices, and methods for conducting highly sensitive assays that employ two binding agents and are useful in detecting specific targets such as antigens. These devices and methods provide the ability to detect minute amounts of the specific target with reduced risk of false positive results.

2 Claims, 2 Drawing Sheets

(52) U.S. Cl.
CPC . *G01N 33/54353* (2013.01); *G01N 33/56911* (2013.01); *G01N 2333/33* (2013.01); *G01N 2469/10* (2013.01)

(58) Field of Classification Search
CPC ............. G01N 33/5306; G01N 33/533; G01N 33/54353; G01N 33/53
USPC ..... 435/7.1, 7.93, 7.94, 7.95, 7.92; 436/524, 436/518, 172, 804
See application file for complete search history.

(56) References Cited

U.S. PATENT DOCUMENTS

| | | | |
|---|---|---|---|
| 5,891,649 A * | 4/1999 | Kidwell | ........... G01N 33/54386 422/504 |
| 6,054,047 A | 4/2000 | Hindsgaul et al. | |
| 2017/0234865 A1 | 8/2017 | Swiss | |

OTHER PUBLICATIONS

Eva Baldrich, Josep Lluis Acero, Gunter Reekmans, Wim Laureyn, and Ciara K. O'Sullivan. Displacement Enzyme Linked Aptamer Assay. Anal. Chem. vol. 77, pp. 4774-4784. 2005 (Year: 2005).*
Sandhu Premjeet Gupta Deepika, Bhardwaj Sudeep,Jain Sonam, Kataria Sahil, Rathore Devashish, Kumar Sunil.Enzyme—Linked Immuno-Sorbent Assay (ELISA) basics and it's application : A comprehensive review, Journal of Pharmacy Research 2011, 4(12), 4581-4583 (Year: 2011).*
Thermo Scientific Avidin-Biotion Technical Handbook, Copyright 2009 (Year: 2009).*
Cox, et al., "Immunoassay Methods," Eli Lilly & Company and the National Center for Advancing Translational Sciences, Dec. 24, 2014, pp. 1-44.
Gibbs, "Immobilization Principles-Selecting the Surface," ELISA Technical Bulletin- No. 1, Corning Incorporated, Jul. 2001, pp. 1-8. Web. [Retrieved Jun. 28, 2021].
International Search Report and Written Opinion (PCT/ISA/220, PCT/ISA/210, and PCT/ISA/237) issued in PCT Application No. PCT/US17/17988 dated May 19, 2017 (7 pages).

* cited by examiner

METHODS, COMPOSITIONS AND DEVICES FOR IMPROVING THE SENSITIVITY OF ASSAYS

This application is the national phase entry under 35 U.S.C. 371 of PCT International Application Serial No. PCT/US2017/017988, filed Feb. 15, 2017, which claims the benefit of U.S. Provisional Patent Application No. 62/296,059, filed Feb. 16, 2016, and U.S. Provisional Patent Application No. 62/456,020, filed Feb. 7, 2017, each of which is incorporated herein by reference in its entirety and for all purposes.

FIELD OF THE INVENTION

This invention generally is directed to devices and methods for conducting highly sensitive assays that employ two binding agents and are useful in detecting specific targets such as antigens. These devices and methods provide the ability to detect minute amounts of the specific target with reduced risk of false positive results.

BACKGROUND OF THE INVENTION

Conventional sandwich assays such as ELISA assays are a mainstay of qualitative and quantitative analysis of samples suspected of containing a specific target. In general terms, the specific target is one that possesses at least two separate epitopes that will separately bind to a first and second antibody. The first antibody is typically attached to a solid support and the sample is introduced to the solid support typically as a first aqueous solution. The solution is incubated with the solid support under conditions such that any target in the solution will bind to the first antibody. After incubation, the first solution is removed from the solid support. The solid support is then typically washed. A second solution containing the second antibody is then combined with the solid support and the resulting combination is incubated under conditions where the second antibody binds to a separate epitope on the target. The second antibody contains a detectable label that signals the presence of target on the solid support.

One of the drawbacks of such conventional assays is often an unacceptable level of false positives are generated by the assay due to non-specific binding of the second antibody. One way to reduce the level of false positives is to lower the sensitivity of the assay so that higher concentrations of the target are required to yield a positive result. This is because the degree of non-specific binding is assumed to be a constant. Hence, a higher threshold of target concentration that is above the level of non-specific binding minimizes false positives. This, however, is not an acceptable solution as the increased accuracy of the assay is at the expense of diminished sensitivity.

Accordingly, there is a need to provide highly sensitive assays without increasing the number of false positives.

SUMMARY OF THE INVENTION

This invention is predicated, in part, on the discovery of devices and methods that increase the sensitivity of assays using two antibodies. In many cases, this increase in sensitivity is accomplished while either maintaining or reducing the number of false positives. The methods, devices and compositions described herein are useful in assessing the presence of disease components in, e.g., blood, urine, tissue sample or cells, and the like especially derived from a human suspected of having a disease. The inventions described herein are not intended for use in assays for quality control of foodstuffs, e.g., by testing a food source, e.g., cows, pigs, sheep, horses, or plants, or a food product at any stage of processing, storage, or serving for the presence of an agent, e.g., a contaminant, a pathogen, e.g., viruses and bacteria, or a microbial toxin, that causes a food borne illness.

Specifically, the methods and devices of this invention employ a first binding agent having specificity to a selected target such as an antigen. The first binding agent is preferably covalently bound to a suitable solid support. The methods and devices of this invention also provide for a complex comprising a second binding agent non-covalently bound to a surrogate ligand that, in turn, is covalently attached to an applicator wherein the second binding agent has attached thereto a detectable label. The applicator is capable of either manually or robotically contacting the solid support at least in a portion of the area where the first binding agent is bound.

When the applicator with the bound complex is applied to the support, the surrogate ligand acts as an intermediary target and binds to the second binding agent. The surrogate ligand is designed to remain bound to the second binding agent in all cases other than when contacted to the target bound to the first binding agent. That is to say in the presence of both the surrogate ligand and the target, the target due to its higher binding affinity "wins" as it displaces the surrogate ligand and binds the second binding agent removing it from the applicator. The second binding agent can then be detected on the support indicating the presence of the target. This is contemplated to significantly improve sensitivity of the assay and/or reduce the number of false positives arising in the assay due to non-specific binding.

The increase in assay sensitivity is accomplished by selecting a surrogate ligand that has a defined binding affinity to the second binding agent that is defined by a dissociation constant that is at least about $1\times10^{-5}$. In addition, the dissociation constant of the surrogate ligand is selected to be at least about $1\times10^{-2}$ or at least $1\times10^{-3}$ lower than the dissociation constant for the second binding agent and the target. In one preferred embodiment, the surrogate ligand has a dissociation constant with the second binding agent of $1\times10^{-7}$ or less and the target has a dissociation constant with the second binding agent that evidences more robust binding by a factor of at least $1\times10^{-2}$ tighter such that the dissociation constant of the target and second binding agent is $10^{-9}$ or less. In another embodiment, if the surrogate ligand—second binding agent's dissociation constant is $1\times10^{-8}$, then the dissociation constant for the target—second antibody is $1\times10^{-10}$ or less. Such differential binding constants ensure that the second antibody will be removed from the surrogate ligand in the presence of target bound to the first antibody. Moreover, the required dissociation constant for the surrogate ligand—second antibody ensures that non-specific binding of the second antibody is either significantly reduced or eliminated. This combination of properties allows for enhanced specificity and/or reduced false positives in the assay.

It should be noted that any binding agents (first or second) that are specific to the target can be used in this invention including, by way of example, antibodies, antibody fragments, aptamers, biotin, avidin, DNA, RNA, and the like. Likewise, any type of label can be used in this invention including fluorescent labels, radioactive labels, enzymes, pH indicators, and the like.

In one of its device aspects, this invention provides for a device comprising a complex comprising an applicator that is bound to a surrogate ligand that, in turn, is non-covalently complexed to a second binding agent wherein the second binding agent has attached thereto a detectable label. The surrogate ligand may be bound to the applicator either covalently or non-covalently. If the surrogate ligand is bound to the applicator non-covalently the dissociation constant is, e.g., $10^{14}$ or less or $10^{15}$ or less. In any case the surrogate ligand has an affinity for the applicator that is at least 10 fold, 100 fold or 1000 fold greater than its binding affinity for the second binding agent such that the surrogate ligand remains bound to the applicator when the applicator is contacted with the support except when the support contains target bound to the first binding agent.

In one of its method aspects, this invention provides for a method for enhancing sensitivity of an assay which comprises a first and second binding agent wherein the first binding agent binds to a target at a first epitope and said second binding agent binds to the target at a second epitope wherein said second binding agent contains a label which permits determination of the presence of said target wherein said method comprises:

a) contacting said first binding agent with a sample suspected of containing the target under conditions wherein said target, if present, forms a first binding pair with the first binding agent wherein said first binding agent is bound to a support;

b) forming a second binding pair between said second binding agent and a surrogate ligand wherein the binding affinity of said surrogate ligand to the second binding agent is less than that of the target to said second binding agent;

c) contacting said second binding pair with said support and maintaining said contact under conditions wherein said surrogate ligand is displaced from the second binding agent by the target so as to form a first binding agent-target-second binding agent complex when said target is present in said sample; and d) identifying the presence of the target by the presence of the signal generated by the label bound to the second binding agent in said first binding agent-target-second binding agent complex.

In one embodiment, the surrogate ligand is covalently attached to an applicator. In one embodiment, the applicator is an aqueous absorbent pad or sponge. In one embodiment, the applicator is capable of either manually or robotically contacting the solid support at least in a portion of the area where the first binding agent is bound.

In one embodiment, the binding affinity of the second binding agent to the target is at least 100 times greater than the binding affinity of the binding agent to the surrogate ligand and preferably at least 1000 times greater.

In one embodiment, the first and second binding agents are independently selected from the group consisting of antibodies, antibody fragments, aptamers including DNA, RNA, and peptides, and the like. In one embodiment, the first and second binding agents are antibodies and preferably monoclonal antibodies.

In one embodiment, the surrogate ligand is covalently bound to an applicator such as a sponge or other bibulous material. In one embodiment, the surrogate ligand is selected from the group consisting of antibodies, antibody fragments, aptamers including DNA, RNA, and peptides. In one embodiment, the binding specificity or binding affinity of the second binding agent, e.g., and antibody, to the target is at least 10 times stronger than its binding specificity or affinity to the surrogate ligand and, more preferably, from 100 to 10,000 times. Both the target and the surrogate ligand bind to the second binding agent and as such the second binding agent remains bound to the surrogate ligand prior to application, but upon contact with the target the second binding agent binds to the target and is detected on the support. As such, the surrogate ligand remains bound to the second binding agent unless the target is present.

This disclosure further relates to a method for reducing non-specific binding in an assay to determine the presence and/or abundance of a target molecule or cell (target), the method comprising applying a binding agent to a sample comprising the molecule or cell of interest, wherein the binding agent is bound to a surrogate ligand prior to application to the sample. In one embodiment, the binding affinity of the binding agent for the surrogate ligand is between about 1/10 and about 1/10,000 of the binding affinity for the target, e.g., a molecule or cell of interest.

In one embodiment, the assay employs two binding agents specific for the target, e.g., a molecule or cell. In one embodiment, the surrogate ligand is attached to an applicator. In one embodiment, the surrogate ligand is free (in combination with the binding agent) in solution. In one embodiment, the surrogate ligand is not associated with the binding agent prior to application, but is applied to the sample after application of the binding agent. For example, the second binding agent containing a detectable label can be applied into the solution contacting the solid support, the first binding agent and any target found in the sample. After incubation, the solid support is contacted with an applicator containing the surrogate ligand covalently bound thereto to remove any weakly bound second binding agent/label that, for example, is held onto the solid support by non-specific binding. The amount of remaining second binding agent is indicative of the presence or absence of the target.

In one embodiment, the label is selected from the group consisting of enzymatic signaling molecules, fluorescent signaling molecules, radioactive signaling molecules, signaling molecules that produce visible light, and chemiluminescent signaling molecules.

In one embodiment, the second binding pair is covalently attached through the surrogate ligand to an applicator, which may be a moveable support. In a preferred embodiment, the applicator is selected from the group consisting of a sponge, a pad, a swab, and a bead. The particular material of the applicator employed is not critical provided it binds or can be functionalized to bind the surrogate ligand, including e.g., glass, latex, polystyrene or polypropylene.

The presence of nanogram, picogram or lesser amounts of a target in a sample can be determined by the methods, compositions and devices of this invention. The high specificity of the disclosed methods also reduces the incidence of false positives.

DETAILED DESCRIPTION OF THE INVENTION

As described above, this invention is directed to assays, methods and devices for increasing the sensitivity of assays employing two binding agents.

Before this invention is disclosed and described, it is to be understood that the aspects described below are not limited to specific compositions, methods and/or devices of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings.

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (-) 10%, 5%, 1%, or any subrange or subvalue there between.

The term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "sensitivity" refers to the ability of an assay to detect smaller quantities of target without an unacceptable rate of false positives. In one embodiment, the sensitivity of the assays described herein are increased by 10 fold or by 20 fold or by 30 fold or by 50 fold or by 100 fold or more over conventional sandwich assay technology.

The term "target" or "target ligand" refers to any and all antigens, pathogens, peptides, proteins, including for example enzymes and autoantibodies, cells, cellular debris, toxins, and the like that are detectible by conventional assays and have at least two distinct epitopes to which binding agents can bind.

The term "binding agent" as it relates to first and second binding agents refers to any and all agents capable of specific binding to an epitope on the target. Suitable binding agents include antibodies, antibody fragments, DNA, RNA, peptides, proteins, aptamers, avidin/biotin, and the like. The first binding agent is selected to be specific for binding to a first epitope on the target. The second binding agent is selected to be specific to a second epitope on the target and both the first and second binding agents are selected as having a strong binding affinity to their respective epitopes on the target.

Binding affinities are typically measured in the binding agent's dissociation constant to the target. Dissociation constants are defined for a reaction where:

where A is the target and B is a binding agent. As the binding agent is complexed with the target through non-covalent interactions (e.g., hydrophobic, hydrophilic and ionic), the complex is in equilibrium with its dissociated components. The equilibrium for association/dissociation is determined by the formula:

$$K_d = \frac{[A]^x[B]^y}{[A_xB_y]}$$

where $K_d$ is the dissociation constant, [A] and [B] represent the concentrations of the dissociated components of the complex $A_xB_y$, and $[A_xB_y]$ represents the concentration of the complex. So, the lower the $K_d$, the greater the binding affinity of the binding agent is for the target. Hence, a dissociation constant of $1\times10^{-8}$ evidences a binding affinity of a binding agent that is 100 times weaker that a binding agent having a dissociation constant of $1\times10^{-10}$.

The term "binding specificity" refers to the ability a binding agent to bind preferentially to a selected epitope on the target to the exclusion of other epitopes on the target. Binding specificity can be measured by determining the dissociation constant of the binding agent for its selected epitope on the target as compared to other epitopes. Generally, binding agents should have dissociation constants for the target epitope of at least $1\times10^{-8}$ and preferably at least $1\times10^{-10}$ whereas other epitopes on the target will have a significantly weaker dissociation constant such as no more than $1\times10^{-6}$ or $1\times10^{-4}$. As the binding agent is used in excess relative to the target.

Specific binding means that the binding agent binds to the designated target with little to no non-specific binding.

The term "label" refers to any chemical, biological or isotopic entity such as a compound, an atom, an enzyme, etc. that produces or can be modified to produce a detectable signal. Examples of labels include fluorescent labels such as fluorescein, ethidium bromide, pyranine, cyanine, hydroxycoumarin, methoxycoumarin, Alexa fluor, aminocoumarin, Cy2, FAM, Alexa fluor 488, fluorescein FITC, Alexa fluor 430, Alexa fluor 532, HEX, Cy3, TRITC, Alexa fluor 546, Alexa fluor 555, R-phycoerythrin, Rhodamine Red-X, Tamara, Cy3.5 581, Rox, Alexa fluor 568, Red 613, Tex Red, Alexa fluor 594, Alexa fluor 633, Allophycocyanin, Alexa fluor 633, Cy 5, TruRed, Alexa fluor 680, Cy7, DAI, Hoechst 33258, SYTOX blue, Hoescht 33342, YOYO-1, SYTOX green, TOTO 1, TO-PRO-1, SYTOX orange, Chromomycin A3, Mithramycin, Propidium iodide, and the like. Examples of isotopic labels include iodide 135 and hydrogen 3. Examples of biological labels include chemoluminescence, enzymes such as horse-radish peroxidase, and the like. The particular label used is not critical provided that it produces or is modified to produce a detectible signal. In one embodiment, the label is covalent bound to the second binding agent.

The term "detectible signal" refers to any signal that can be captured any means such as by visual or electronic surveillance of the sample under conditions that generate the signal. In one embodiment, the The term "surrogate ligand" refers to a molecule that is not the target but binds to the second binding agent with a high level of binding affinity but, in all cases, at a binding affinity at least 10 time less than the second antibody binds to the target. As so used, the surrogate ligand acts as an intermediary binding molecule to the second binding agent and is designed to remain bound to the second binding agent in all cases other than when the second binding agent is contacted to the target bound to the first binding agent. In one embodiment, the surrogate ligand has a binding affinity to the second binding agent that is measured by a dissociation constant of up to about $1 \times 10^{10}$ but, in all cases, the binding affinity of the surrogate ligand to the second binding agent is less than that of the target to the second binding agent. Suitable surrogate ligands can be proteins, peptides, DNA, RNA, aptamers, antibodies, antibody fragments, partially denatured antibodies and antibody fragments, and the like.

The term "applicator" refers to any material to which the surrogate is covalently bound thereto. Such applicators preferably are deformable and hydroscopic. In one preferred embodiment, the applicator material includes bibulous materials such as sponges, pads, cotton balls, and the like. The applicator can be manually applied to the first binding agent and target (if present) or the applicator can be positioned in a robotic device that interfaces with the first binding agent and target (if present).

The term "solid support" refers to any support that binds the first binding agent. Such supports preferably include beads, plates, slides, test tubes, and the like. The particular solid support employed is not critical provided it binds or has been functionalized to covalently or non-covalently bind to the first binding agent, including, e.g., glass, latex, polystyrene, and polypropylene.

Methodology

Test Components

In one embodiment, the methods employ a solid support such as those having surface functional groups so as to covalently link the first binding agent thereto. Such solid supports are well known in the art and many of which are commercially available. For example, amino functionalized microbeads as well as carboxyl functionalized microbeads are available from Spherotech, Inc., 27845 Irma Lee Circle, Unit 101, Lake Forest, Ill. 60045, USA. The amino functionalized microbeads readily react with carboxyl groups on the first binding agent so as to provide a covalent amide linkages. Suitable carboxyl groups include aspartic and glutamic amino acid side chains found in the binding agents. The carboxyl functionalized microbeads readily react with amino groups on the first binding agent so as to provide covalent amide linkages. Suitable amino groups include lysine amino acid side chains found in the binding agents. The chemistry to form such covalent bonds is exceptionally well known in the art and follows peptidic amide formation conventionally used in peptide synthesis.

The surrogate ligands employed herein are readily identified by conventional screening of a library of putative ligands and then defining ligands that have the desired dissociation constant with the second binding agent. Such conventional screening involves a library of putative ligands such as aptamers, antibodies, antibody fragments, DNA, RNA, peptides, proteins and the like. Customized ligand libraries, wherein the ligand may be e.g., proteins, peptides, DNA, RNA, aptamers, antibodies, antibody fragments, are routinely prepared using commercially available reagent kits and/or commercial services offered by, e.g., Sigma Aldrich Chemical Company, ABclonal (Woburn, Mass.), and Pepscan, (The Netherlands). The relative dissociation constant for each member of the library is assessed relative to the second binding agent. In one example, frontal affinity chromatography can be used to identify the relative binding affinity of the library members to the second binding agent. In particular, a library of known putative ligands is introduced to a column containing the second binding agent. The rate of introduction is controlled so that initially any ligand that binds to the second binding agent will bind. The mixture is continued to be introduced and at some point, all of the second binging agent is bound with putative ligands. As even more of the mixture is introduced, the weakest binder falls off and is identified by electrospray mass spectroscopy. The procedure is followed until one by one each of the putative ligands is recovered and identified by electrospray mass spectroscopy. When the putative ligands are recovered and identified, one then has a rank order of the relative binding affinities of each of the putative ligands relative to the second binding agent. Subsequent identification of the dissociation constants of the relevant putative ligands will identify those that are candidates to be selected as the surrogate ligand. The selection is based on the desired relative binding affinities between the second binding agent and the surrogate ligand. If the ratio of binding affinities is 10:1 (second binding agent: surrogate ligand) the surrogate ligand selected will be different as compared to a ratio of 100:1. This procedure is well established and disclosed in U.S. Pat. No. 6,054,047 which is incorporated herein by reference in its entirety.

The surrogate ligand is then bound to the applicator via conventional chemistry. For example, any amino groups on the surrogate ligand can react with carboxyl groups on the applicator to form amide linkages the chemistry of which is well known in solid phase peptide synthesis. Likewise, any carboxyl groups on the surrogate ligands can react with amino groups on the applicator to again form amide linkages. Hydroxyl functional groups on the surrogate ligands can react with carboxyl groups on the applicator to form ester linkages. Alternatively, hydroxyl and amino groups on the surrogate ligand can react with isocyanate to form carbamate and urea linkages or, alternatively, can react with isothiocyanate to form thiocarbamate and thiourea linkages. The chemistry of these reactions is exceptionally well known.

It is also envisioned that the surrogate ligand could be bound to the applicator via a non-covalent linkage. One example of suitable non-covalent binding includes avidin (or streptavidin)-biotin where either member of this binding pair is bound directly or indirectly to the applicator and the other member is bound to the surrogate ligand. Likewise, aptamers can be prepared that have high non-covalent binding affinities to the surrogate ligand while being bound to the applicator. Biotinylation and avidin conjugation reagents and kits for targeting specific functional groups or residues are readily available in the art, e.g., from ThermoFischer Scientific and abcam (Cambridge, Mass.)

Selection of the second binding agent is very well known in the art as is the attachment of detectable label(s) onto that agent. In many cases, the second binding agent is an antibody, and antibody fragment, a peptide or a protein. In such cases, detectable labels having isothiocyanate group fluorescein 5-isothiocyanate and rhodamine isothiocyanate are both commercially available. Isotopic iodine 131 can be coupled to a compound that can bind to the second binding agent and the resulting compound becomes a detectible label. The use of iodine 131 in such a manner is very well established in the art. Enzymes and other labels are very well known.

As supports, first binding agents, seconding binding agents and labels are well known in the art, such materials, by themselves, do not form a part of the composition aspects of this invention.

The methods of this invention involve several steps the order of which can be altered by those skilled in the art as appropriate without loss of functionality or specificity.

Assay Steps

As noted above, this invention provides for a method for enhancing sensitivity of an assay which comprises a first and second binding agent wherein the first binding agent binds to a target at a first epitope and said second binding agent binds to the target at a second epitope wherein said second binding agent contains a label which permits determination of the presence of said target. This method comprises:
  a) contacting said first binding agent with a sample suspected of containing the target under conditions wherein said target, if present, forms a first binding pair with the first binding agent wherein said first binding agent is bound to a support;
  b) forming a second binding pair between said second binding agent and a surrogate ligand wherein the binding affinity of said surrogate ligand is less than that of the target to said second binding agent;
  c) contacting said second binding pair with said support and maintaining said contact under conditions wherein said surrogate ligand is displaced from the second binding agent by the target so as to form a first binding agent-target-second binding agent complex when said target is present in said sample; and
  d) identifying the presence or absence of the target by the presence or absence of the signal generated by the label bound to the second binding agent in said first binding agent-target-second binding agent complex.

As noted above, it is necessary that the second binding agent has a binding affinity to the target that is greater than the binding affinity of the second binding agent to the surrogate ligand.

In the assay as described above, a sample, typically an aqueous sample, suspected of containing the target is contacted with a solid support having bound thereto a first binding agent specific for that target. Binding to the support is typically covalent binding but non-covalent binding can be used provided that it retains the first binding pair on the support. It is contemplated that the first binding agent may be non-covalently bound to the support such that the dissociation constant of the first binding agent to the support is $10^{-14}$ or less, or $10^{-15}$ or less. One example of suitable non-covalent binding includes avidin-biotin where either member of this binding pair is bound directly or indirectly to the support and the other member is bound to the first binding agent. Likewise, aptamers can be prepared that have high non-covalent binding affinities to the first binding agent while being bound to the solid support.

Once the sample suspected of containing the target is contacted with the support, contact is maintained for a sufficient period of time and under conditions where target present in the sample will bind to the first binding agent. Such conditions are well known in the art and include temperatures from about 10° to about 40° C. for a period of time sufficient to effect binding. Typically such times run from about 0.1 to about 24 hours. Subsequently, the sample is removed from the solid support that is then washed to remove any contaminants remaining thereon.

The solid support is then contacted with an applicator at the site containing the first binding agent. The applicator has associated therewith a complex comprising a second binding agent non-covalently bound to a surrogate ligand that, in turn, is covalently attached to the applicator. The second binding agent has attached thereto a detectable label. The applicator is capable of either manually or robotically contacting the solid support at least in a portion of the area where the first binding agent is found. Contacting is done under conditions where the second binding agent contacts the first binding agent. In one preferred embodiment, the applicator is hydrated and deformable so that applicator contact with the first binding agent and any target bound thereto will be enhanced and hydration of the applicator allows for maximum contact.

Contacting is maintained under conditions where the target can bind to the second binding agent. Such conditions preferably include temperatures from about 10° to about 40° C. for a period of time sufficient to affect binding. Typically such times run from about 0.1 to about 24 hours. Subsequently, the applicator is removed the solid support which is then washed to remove any contaminants remaining on the support.

In this process, the surrogate ligand acts as an intermediary binding target to the second binding agent and is designed to remain bound to the second binding agent in all cases other than when contacted to the target bound to the first binding agent. That is to say that under the conditions of the methods described herein, the surrogate ligand acts to retain the second binding agent on the applicator except when contacted with a target. This is contemplated to significantly improve sensitivity of the assay and/or reducing the number of false positives arising in the assay due to non-specific binding.

Alternatively, the second binding agent is not associated with the surrogate during its initial contact with the solid support having bound thereto the first binding agent and any target present. Rather, it can be applied as part of a solution that is added to the solid support. For example, the second binding agent containing a detectable label can be applied into the solution contacting the solid support, the first binding agent and any target found in the sample. After incubation and binding of the second binding agent to the target (if any), the solid support is contacted with an applicator containing the surrogate ligand covalently bound thereto. Any non-specifically bound second binding agent will be retrieved from the surface of the support due to the enhanced binding affinity accorded by the surrogate ligand whereas any second binding agent bound to target/first binding agent will remain on the support surface due to the enhanced binding affinity of the second binding agent to the target relative to its binding affinity to the surrogate. The amount of remaining second binding agent detected on the support is indicative of the presence or absence of the target.

As provided above, the second binding agent contains one or more detectible labels. If target is present and has bound to the first binding agent, binding of the second binding agent to the target will carry with it detectible labels that permit detection of the signal generated by these labels. In one embodiment, the signal generated can be readily assessed as in the case of radioactive isotopes, fluorescent labels and the like. In one embodiment, the signal generated is assessed after modifying the label so as to permit signal generation. For example, if pH indicators are employed as the detectible label and the indicator provides an intense color at pH 3 or less, adjusting the pH of the solution will permit signal generation. Similarly, the use of enzymes as labels merely require the addition of enzyme substrates to generate the desired detectible signal. All of such modifications are well within the purview of the skilled artisan.

In some cases, it may be advantageous to reduce the amount of non-specific binding by conventional methods such as by application of albumin to the surface of the support. The art provides a proliferative number of conditions to reduce non-specific binding in assay protocols by pretreatment of the support.

After completing the assay described above, the support is placed into a position where the presence or absence of label is readily determined. The presence of label corresponds to a positive result whereas the absence of label corresponds to a negative result. In addition, in many cases, the presence of label can be correlated to the intensity of the signal generated thereby providing a quantitative evaluation of the amount of target present. Such correlation is readily made by use of a concentration table using known concentrations of target in the assay and correlating the intensity of the signal generated to the concentration of the target responsible for generating that signal. The signal intensity generated in a given assay is then superimposed on the table and a concentration of the amount of target in that sample can be assessed.

Utility

The methods, devices and compositions described herein are useful in assessing the presence of disease components in, e.g., blood, urine, tissue sample or cells, and the like especially derived from a human suspected of having a disease. Such components include the microbes or cells responsible for the disease, toxins produced by the microbes or cells, and biological markers of the disease. Alternatively, the assays described herein can be used to provide highly accurate evaluation of the patient's hormone level, the presence of genetic components in the patient's genome as well as standard assays for pregnancy. In short, this invention provides a means to enhance the sensitivity and/or reduce the number of false positives in any assay that employs two binding agents, such as in ELISA assays. The inventions described herein exclude assays for testing a food source, e.g., cows, pigs, sheep, horses, or plants, or a food product at any stage of processing, storage, or serving for the presence of an agent, e.g., a contaminant, a pathogen, e.g., viruses and bacteria, or a microbial toxin, that causes a food borne illness.

In an alternative approach, there is provided herein is a method for reducing background signaling in a assay which comprises a first and second antibody wherein the first antibody binds to a target ligand at a first epitope and said second antibody binds to the target ligand at a second epitope wherein said second antibody contains a signaling molecule which permits determination of the presence of said target ligand wherein said method comprises:
  a) contacting said first antibody with a sample suspected of containing the target ligand under conditions wherein any target ligand present forms a first binding pair with the first antibody;
  b) forming a second binding pair between said second antibody and a surrogate ligand wherein the binding affinity of said surrogate ligand is less than that of the target ligand to said second antibody;
  c) contacting said second binding pair with the first antibody which formed a first binding pair in the presence of the target ligand;
  d) maintaining said contact for a sufficient period of time to allow displacement of the said surrogate ligand by said target ligand so as to form a third binding pair in the presence of the target ligand;
  e) isolating the first antibody and any third binding pair so that any background signaling due to the presence of unbound second antibody is reduced; and
  f) identifying the presence of the target ligand by the presence of the signal generated by the signaling molecule bound to the second antibody in said third binding pair.

The following examples are provided merely to illustrate the invention and do not serve in any manner as a limitation thereto.

Example 1

Figure 1:
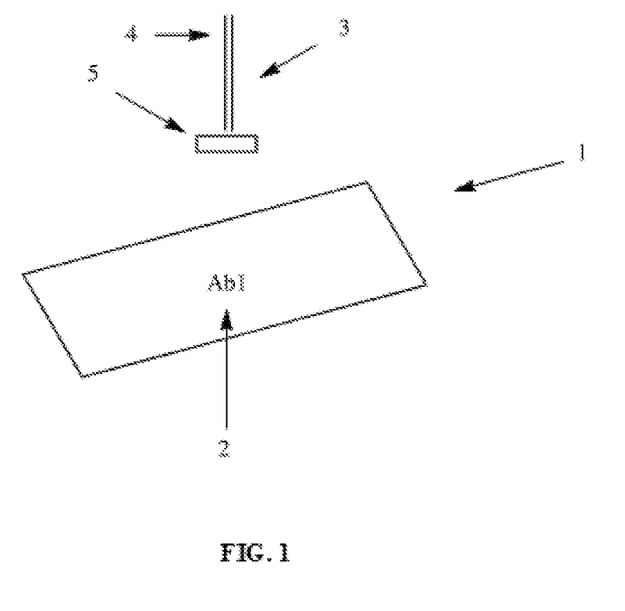
FIG. 1 illustrates one example of the methodology disclosed herein.

One example of the devices and compositions used in assay protocol is illustrated in FIG. 1. In that figure, a solid support (1) has a first binding agent covalently bound thereto in the form of first antibody (Ab1) (2). The antibody has a binding specificity to the toxin produced by *C. difficile* that is commonly associated with antibiotic associated diarrhea in nursing homes. The binding affinity of the first antibody is measured by a dissociation constant of $1\times10^{-10}$ or stronger.

Centered above solid support (1) is an applicator (3) containing an arm (4) and an application device (5) which can be any device as described herein including a microsponge. The applicator (3) is removable either by manually or automated means.

Figure 2:
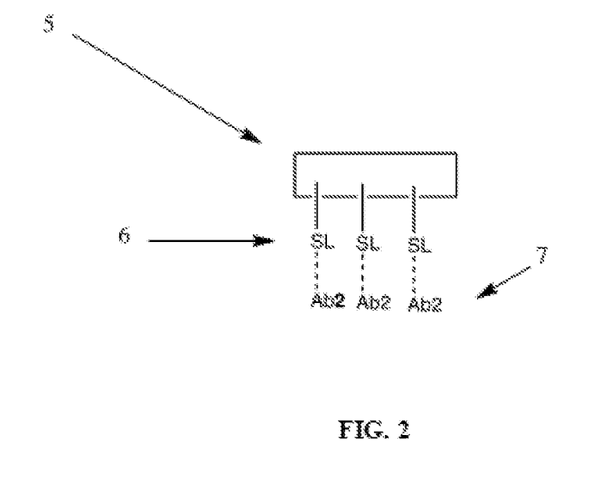
FIG. 2 illustrates one example of the application device (5) having attached thereto a plurality of surrogate ligands (SL) (6).

The application device (5) is further elaborated on in FIG. 2. There covalently attached to the application device are a plurality of surrogate ligands (SL) (6). The surrogate ligands are non-covalently bound to a second binding agent in the form of a second antibody (Ab2)(7) that is labeled (the label is not shown). The second antibody (Ab2) is retained in place by a binding affinity to the surrogate ligand as measured by a dissociation constant of $1\times10^{-7}$. The second antibody (7) has a binding affinity to the target of $1\times10^{-9}$ or stronger such that the second antibody's binding affinity to the target is approximately 100 times or more greater than the second antibody's binding affinity to surrogate ligand.

Example 2

Figure 3A:
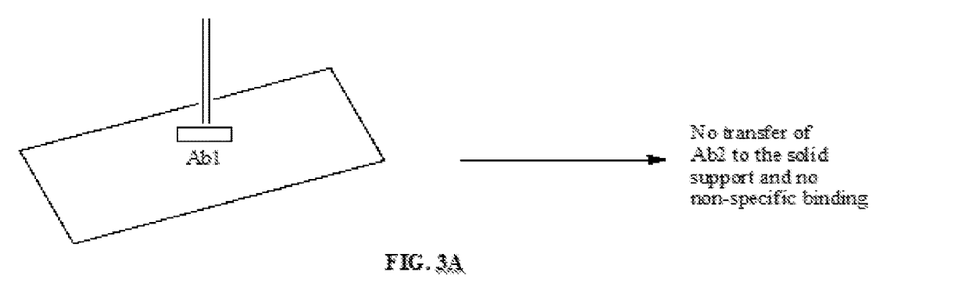
FIG. 3 illustrates an embodiment of the assay in use.

This example illustrates the assay in use. Specifically, in FIG. 3A, solid support (1) contains antibody Ab1 covalently bound to the support, but no target is present. The applicator, Ab1, Ab2, surrogate ligand and target are as described in Example 1. As such, after contacting the applicator to solid support (1), antibody Ab2 remains on the applicator as the surrogate ligand's binding affinity for Ab2 is sufficient to inhibit non-specific binding of Ab2 to non-target antigens.

Figure 3B:
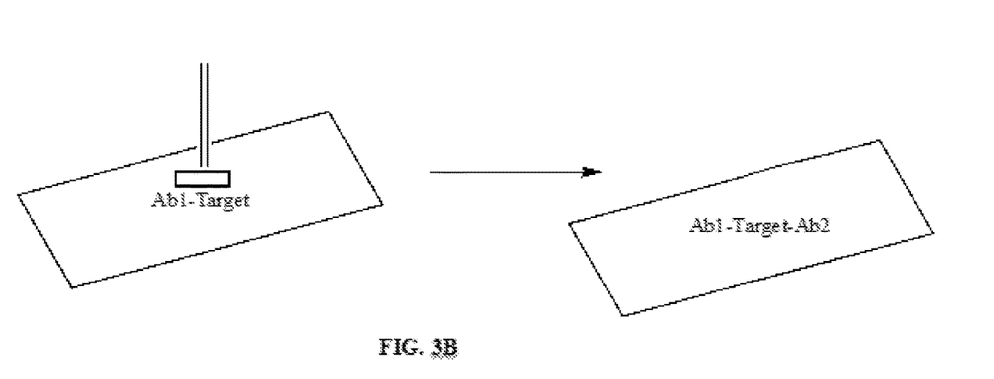

In FIG. 3B, solid support (1) contains antibody Ab1 and the target. As such, after contacting the applicator to solid support (1), antibody Ab2 is extracted from the surrogate ligand due to the significantly greater binding affinity that the target has to Ab2 relative to the binding affinity of the surrogate ligand to Ab2.

The above examples illustrate one embodiment of this invention. Other embodiments are readily discernible by the contents of this application and the skill of the art. Such other embodiments are included within the scope of the claimed invention.

The invention claimed is:

1. An assay method which comprises:
    selecting a first and second binding agent wherein the first binding agent binds to a target at a first epitope and is bound to a support and said second binding agent binds to the target at a second epitope at a first binding affinity and wherein said second binding agent contains a detectable label which permits determination of the presence of said target;
    contacting said first binding agent with a sample suspected of containing the target under conditions wherein said target, if present, forms a first binding pair with the first binding agent bound to said support;
    selecting a surrogate ligand which has a second binding affinity to said second epitope wherein said second binding affinity ranges from $1/10$ to $1/10,000$ times weaker than said first binding affinity;
    covalently attaching a plurality of surrogate ligands to an applicator;
    forming a second binding pair between said second binding agent and said surrogate ligand;
    contacting said applicator with said second binding pair to said support and maintaining said contact under conditions wherein the presence of said target complexed to said first binding agent will capture said second binding agent from said surrogate ligand so as to form a first binding agent-target-second binding agent complex;
    removing said applicator from said surface; and
    identifying the presence of the target by the presence of the label bound to the said second binding agent in said first binding agent-target-second binding agent complex.

2. The method of claim 1 wherein the label is a fluorescent label, a radioactive label, an enzyme, or a pH indicator.

* * * * *